United States Patent [19]

Benavides et al.

[11] Patent Number: 5,543,421
[45] Date of Patent: Aug. 6, 1996

[54] METHOD OF TREATMENT OF PERIPHERAL NEUROPATHIES AND CENTRAL NEURODEGENERATIVE DISEASES

[75] Inventors: Jésus Benavides, Chatenay Malabry; Badia Ferzaz, Antony; Pascal George, Saint Arnoult en Yveline; Bernard Scatton, Villebon sur Yvette, all of France

[73] Assignee: Synthelabo, Le Plessis Robinson, France

[21] Appl. No.: 327,595

[22] Filed: Oct. 24, 1994

[30] Foreign Application Priority Data

Jul. 29, 1994 [FR] France .................... 94 09410

[51] Int. Cl.⁶ .................... A61K 31/445
[52] U.S. Cl. .................... 514/317
[58] Field of Search .................... 514/317

[56] References Cited

U.S. PATENT DOCUMENTS

| | | | |
|---|---|---|---|
| 5,089,506 | 2/1992 | Gray et al. | 514/325 |
| 5,118,675 | 6/1992 | Jirkovsky et al. | 514/80 |
| 5,252,584 | 10/1993 | Carling et al. | 514/312 |

FOREIGN PATENT DOCUMENTS

| | | |
|---|---|---|
| 5733 | 9/1966 | France . |
| 2678269 | 6/1991 | France . |
| WO92/03137 | 3/1992 | WIPO . |
| WO95/01096 | 1/1995 | WIPO . |

OTHER PUBLICATIONS

J. Pharmacol Exp Ther, Feb. 1992, vol. 260, No. 2, pp. 925–932, Shalaby et al, "Neuroprotective effects of the N–methyl . . . ".

J. Pharmacol Exp Ther, Feb. 1991, vol. 256, No. 2, pp. 506–512, Sonsalla PK et al, "Competitive and noncompetitive antagonists . . . ".

Chemical Abstracts, vol. 120, No. 7, Feb. 1994, Abstract No. 69300m, p. 75, column 1 & p. 359, vol. 11, No. 6, "Tamura, 1991".

J. Pharmacol. Exp. Ther., vol. 247, No. 3, 1988, pp. 1211–1221 Gotti et al, "Ifenprodil and SL82.0715 as cerabral anti–. . . ".

Encephale, vol. 18, No. 3, 1992, pp. 271–279, Krebs, "Acides aminés excitateurs, une nouvelle classe de neurotransmetteurs . . . ".

New Engl. J. Med., vol. 330, No. 9, pp. 613–622, Mar. 1994, Lipton et al, "Mechanisms of disease: Excitatory amino acids . . . ".

Eur. neuropsychopharmacol, 1993, vol. 3, No. 3, pp. 184–185, Meldrum, B.S., "Anti–excitatory amino acid approach in the . . . ".

G. Buyuk, "Chemie für Pharmazeuten II", 178, Georg Thiem Verlag, Stuttgart, pp. 29–33.

Primary Examiner—Marianne M. Cintins
Assistant Examiner—William R. A. Jarvis
Attorney, Agent, or Firm—Jacobson, Price, Holman & Stern, PLLC

[57] ABSTRACT

Ifenprodil and its enantiomers are disclosed for the preparation of medicines useful for the treatment of peripheral neuropathies and chronic neurodegenerative diseases of the central nervous system.

2 Claims, No Drawings

METHOD OF TREATMENT OF PERIPHERAL NEUROPATHIES AND CENTRAL NEURODEGENERATIVE DISEASES

The present invention concerns the use of ifenprodil and its enantiomers for the preparation of medicines useful for the treatment of peripheral neuropathies and central neurodegenerative diseases.

Ifenprodil, or (±)-erythro-1-(4-hydroxyphenyl) 2-(4-phenylmethyl-1-piperidyl)propanol, a compound with the following structure:

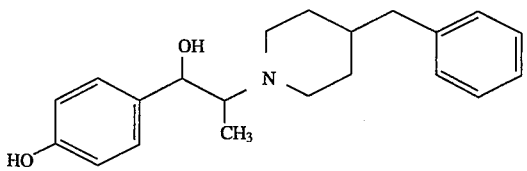

has been described together with its vasodilator properties in U.S. Pat. No. 3,509,164.

Its cerebral anti-ischemic activity has been disclosed in J. Pharmacol. Exp. Ther. 247, 1211 (1988) and in Brain Research 522, 290 (1990).

Ifenprodil has undergone new pharmacological studies which have demonstrated its neurotrophic properties.

More specifically, the stimulation by ifenprodil of the regeneration of the sciatic nerve in the rat was studied in vivo after a local freezing lesion.

Freezing lesion destroys sciatic nerve fibres and results in a wallerian degeneration both at the site of the lesion and in more distal parts. This kind of lesion does not alter the nerve sheaths allowing for reproducible nerve regeneration. The regeneration process begins on the proximal side a few hours after the lesion.

The rate of regeneration of sensory fibres was measured by a pinch-test 8 days after the lesion.

Adult male rats (250 g body weight) of the Sprague-Dawley strain were used. Rats were anaesthetized with sodium pentobarbital (60 mg/kg), the thigh skin was disinfected with ethanol and an incision was made at the level of the junction of femoral biceps. The sciatic nerve was approached by separating the Lateralis and Biceps femoralis muscles. The site of the lesion was marked by a microsuture (Black Ethilon thread 10-0) performed on perineurium above the trifurcation of the sciatic nerve. The nerve was lesioned by 6 freezing and thawing cycles using a copper cryode cooled in liquid nitrogen. The wound was closed and treated with an antibiotic (Exoseptoplix®). Animals were housed one per cage and watched over every day.

After surgery, rats were separated into 2 experimental groups of 6 animals each:

lesioned controls receiving an ip injection of 0.1% Tween 80, 10 min, 2 h and 4 h after injury, and then twice a day for the following seven days.

lesioned rats receiving an ip injection of 3 mg/kg of ifenprodil tartrate (2/1) in 0.1% Tween 80, 10 min, 2 h and 4 h after injury, and then twice a day for the following seven days.

Eight days after surgery, rats were lightly anaesthetized and the sciatic nerve was exposed in order to carry out the pinch test. This test consists of gently pinching the nerve with forceps every 0.5 mm starting from the most distal region from the lesion. A reflex response (contraction of the hindlimb muscles) was observed when pinching at the front of the regenerating sensory fibres. After identifying this site with a microsuture, the nerve was dissected out and the distance between the site of the lesion and the distal microsuture was measured under a surgical microscope using a calibrated paper. After dissection, rats were sacrificed by a pentobarbital overdose.

In untreated lesioned animals, a response to pinch test was observed at a distance of 26 mm from the lesion site 8 days after surgery; this length corresponds to the distance travelled by the regenerating sensory fibres during this time.

In rats treated with ifenprodil tartrate (2:1) at the dose of 3 mg/kg ip, the distance covered by sensory fibres was increased by 14.7%.

The results demonstrate that, in vivo, ifenprodil stimulates peripheral nerve regeneration.

This compound can thus be used for the treatment of peripheral neuropathies such as traumatic (nerve severing or crushing), ischemic, metabolic (diabetes, uraemia), infectious, alcoholic, iatrogenic, genetic neuropathies, in diseases involving motor neurons such as spinal amyotrophies and amyotrophic lateral sclerosis and also in the treatment of chronic neurodegenerative diseases involving a degeneration of central nervous system axons (Alzheimer's disease, Parkinson's disease, Multiple sclerosis).

Ifenprodil and its enantiomers can be used in any galenic form, in association with appropriate excipients for oral, parenteral or local administration, for example as tablets, capsules, solutions, transdermal patches, containing 1 to 200 mg of the active substance per unit dose, suitable for the administration of a daily dose of 1 to 200 mg of the active substance.

We claim:

1. A method of treating peripheral neuropathies and central neurodegenerative diseases in a patient in need thereof which comprises administering to said patient a therapeutically effective amount of ifenprodil or an enantiomer thereof.

2. The method of claim 1 wherein the ifenprodil or enantiomer thereof is administered at a dose of 1 to 200 mg per day.

* * * * *